United States Patent [19]

Piatak, Jr. et al.

[11] Patent Number: 5,101,025

[45] Date of Patent: Mar. 31, 1992

[54] RECOMBINANT TRICHOSANTHIN AND CODING SEQUENCE

[75] Inventors: Michael Piatak, Jr., Pleasanton; Theresa P. Chow, Portola Valley, both of Calif.

[73] Assignee: Genelabs Incorporated, Redwood City, Calif.

[21] Appl. No.: 404,326

[22] Filed: Sep. 7, 1989

Related U.S. Application Data

[62] Division of Ser. No. 333,184, Apr. 4, 1989, abandoned.

[51] Int. Cl.$^5$ .................. C07H 17/00; C12N 15/00
[52] U.S. Cl. .................. 536/27; 536/28; 435/320.1; 435/849
[58] Field of Search .................. 536/27, 28; 435/320, 435/849

[56] References Cited

U.S. PATENT DOCUMENTS

| | | | |
|---|---|---|---|
| 4,459,355 | 7/1984 | Cello et al. | 435/172.3 |
| 4,795,739 | 1/1989 | Lifson et al. | 514/8 |
| 4,869,903 | 9/1989 | Lifson et al. | 424/195.1 |

FOREIGN PATENT DOCUMENTS 0286441 10/1988 European Pat. Off.
WO88/09123 12/1988 PCT Int'l Appl.

OTHER PUBLICATIONS

Tsao, S. W. et al., Toxicon 24(8):831 (1986).
Bonnerjea, J. et al., Bio/Technology 4:955 (1986).
Lee, C. C. et al., Science 239:1288 (1988).
Till, M. A. et al., Science 242:1166 (1988).
Gyllensten, U. B. et al., Proc. Natl. Acad. Sci. U.S.A. 85:7652 (1988).
Chow, T. P. et al., J. Biol. Chem. 265(15):8670 (1990).
Ready, M. P. et al., Proteins: Struct. Funct. Genet. 3(1):53 (1988).
Chaudhary, V. K. et al., Nature 335:369 (1988).
Wang, Q. et al., Shiyan Shengwu Xuebao 20(4):515 (1987)—Abstract from Chemical Abstracts.
Zi-Wei, G. et al., ACTA Chimica Sinica 42(9):943 (1984).
Yu, W. et al., Pure and Appl. Chem. 58(5):789 (1986).
Yeung, H. W. et al., Immunopharm. and Immunotox. 9(1):25 (1987).
Yeung, H. W. et al., Int. J. Pep. Prot. Res. 27:325 (1986).

*Primary Examiner*—John W. Rollins
*Attorney, Agent, or Firm*—Peter J. Dehlinger; Gary R. Fabian

[57] ABSTRACT

Disclosed are the entire coding sequence for unprocessed and mature trichosanthin from *Trichosanthes kirilowii*, and primers derived from this coding sequence for use in obtaining the coding sequences of ribosome inactivating proteins which have regions of amino acid sequence identical to those of trichosanthin. Also disclosed is a recombinant trichosanthin protein produced from the coding sequence, and the mature protein with amino-terminal and/or carboxy-terminal extensions.

9 Claims, 13 Drawing Sheets

```
Asp Val Ser Phe Arg Leu Ser Gly Ala Thr Ser Ser Ser Tyr Gly Val Phe Ile Ser Asn 20
Asp Val Ser Phe Arg Leu Ser Gly Ala Thr Ser Ser Ser Tyr Gly Val Phe Ile Ser Asn

Leu Arg Lys Ala Leu Pro Asn Glu Arg Lys Leu Tyr Asp Ile Pro Leu Leu Arg Ser Ser 40
Leu Arg Lys Ala Leu Pro Asn Glu Arg Lys Leu Tyr Asp Leu Pro Leu Ile Arg Ser Ser

Leu Pro Gly Ser Gln Arg Tyr Ala Leu Ile His Leu Thr Asn Tyr Ala Asp Glu Thr Ile 60
Leu Pro Gly Ser Gln Arg Tyr Ala Ile His Leu Thr Asn Tyr Ala Asp Glu <--- --- ---

Ser Val Ala Ile Asp Val Thr Asn Val     Tyr Ile Met Gly Tyr Arg Ala Gly Asp Thr Ser 80
--> Val Ala Ile Asp Val Thr Asn Val<-->Tyr Ile Met Gly Tyr Arg Ala Gly Asp Thr Ser
                              <Asp Ala Gly Leu Pro Arg Asn Ala Val Leu>

A
                               |-----------------------------------|
Tyr Phe Phe Asn Glu Ala Ser Ala Thr Glu Ala Ala Lys Tyr Val Phe Lys Asp Ala Met 100
Tyr Phe Phe Asn Glu Ala Ser Ala Thr Glu Ala Ala Lys Tyr Val Phe Lys Asp Ala Met

-->|
Arg Lys Val Thr Leu Pro Tyr Ser Gly Asn Tyr Glu Arg Gln Thr Ala Ala Gly Lys 120
Arg Lys Val Thr Leu Pro Tyr Ser Gly Asn Tyr Glu Arg Gln Thr Ala Ala Gly Gly

Ile Arg Glu Asn Ile Pro Leu Gly Leu Pro Ala Leu Asp Ser Ala Ile Thr Thr Leu Phe 140
Ile Arg Glu Asn Ile Pro Leu Gly Leu Pro Ala Leu Asp Ser Ala Ile Thr Thr Leu Phe
Leu

Tyr Tyr Asn Ala Asn Ser Ala Ala Leu Met Val Leu Ile Gln Ser Thr Ser Glu 160
Tyr Tyr Asn Ala Asn Ser Ala Ala Leu Met Val Leu Ile Gln Ser Thr Ser Glu
```

Fig. 1

```
                    |<------------ B ------------------------------
Ala Ala Arg Tyr Lys Phe Ile Glu Gln Gln Ile Gly Lys Arg Val Asp Lys Thr Phe Leu¹⁸⁰
Ala Ala Arg Tyr Lys Phe Ile Glu Gln Gln Ile Gly Ser Arg Val Asp Lys Thr Phe Leu

Pro Ser Leu Ala Ile Ile Ser Leu Glu Asn Ser  Trp Ser Ala Leu Ser Lys Gln Ile Gln²⁰⁰
Pro Ser Leu Ala Ile Ile Ser Leu Glu Asn Ser<>Trp Leu Ala Leu Ser Lys Gln Ile Gln
                                            Leu

Ile Ala Ser Thr Asn Asn Gly Gln Phe Glu Ser Pro Val Val Leu Ile Asn Ala Gln Asn²²⁰
Ile Ala Ser Thr Asn Asn Gly Thr Phe Glu Ser Pro Val Val Leu Ile Asn Ala Gln Asn

Gln Arg Val Thr Ile Thr Asn Val Asp Ala Gly Val Val Thr Ser Asn Ile Ala Leu Leu²⁴⁰
Gln Arg <--- --- --- --- --- --- --- --- --- --- --- --- --- --- --- --- --- ---

Leu Asn Arg Asn Asn Met Ala²⁴⁷
--- ---  --> Asn Asn Met Ala
```

Fig. 1 (con't)

```
1   GTT GGA CTC CCN GCT TTG GAC AGT GCC ATT ACC ACT TTG TTT   42
    Val Gly Leu Pro Ala Leu Asp Ser Ala Ile Thr Thr Leu Phe
    Leu Asp Ser ??? Leu Trp Thr Val Pro Leu Pro Leu Cys Phe
    Trp Thr Pro ??? Phe Gly Gln Cys His Tyr His Phe Val Leu

43  TAC TAC AAC GCC AAT TCT GCT GCT TCG GCA CTT ATG GTA CTC   84
    Tyr Tyr Asn Ala Asn Ser Ala Ala Ser Ala Leu MET Val Leu
    Thr Thr Pro Ile Leu Leu Arg His Leu Trp Tyr Ser
    Leu Gln Arg Gln Phe Cys Cys Phe Gly Thr Tyr Gly Thr His

85  ATT CAG TCG ACG TCT GAG GCT GCA AGG TCA AT                116
    Ile Gln Ser Thr Ser Glu Ala Ala Arg Ser
    Phe Ser Arg Arg Leu Arg Leu Gln Gly Gln
    Ser Val Asp Val TER Gly Cys Lys Val Asn
```

Fig. 3A

```
116  ATT GAC CTT GCA GCC TCA GAC GTC GAC TGA ATG AGT ACC ATA  75
     Ile Asp Leu Ala Ala Ser Asp Val Asp TER MET Ser Thr Ile
     Leu Thr Leu Gln Pro Gln Thr Ser Thr Glu TER Val Pro TER
     TER Pro Cys Ser Leu Arg Arg Leu Asn Glu Tyr His Lys

74  AGT GCC GAA GCA GCA GAA TTG GCG TTG TAG TAA AAC AAA GTG  33
     Ser Ala Glu Ala Ala Glu Leu Ala Leu TER TER Asn Lys Val
     Val Pro Lys Gln Gln Asn Trp Arg Cys Ser Lys Thr Lys Trp
     Cys Arg Ser Ser Arg Ile Gly Val Val Lys Gln Ser Gly

32  GTA ATG GCA CTG TCC AAA GCN GGG AGT CCA AC                1
     Val MET Ala Leu Ser Lys Ala Gly Ser Pro
     TER Trp His Cys Pro Lys ??? Gly Val Gln
     Asn Gly Thr Val Gln Ser ??? Glu Ser Asn
```

Fig. 3B

EcoR I
GAATTCAAATATTTTCTGAATAAATATAAATTCATTGTAGAGAAATGATGAGAAAACAAGAACAATTTCAAAAACAAA  80

AAATAAAAAACAAATGGTTTATCAAAGAAGCCCGAATTTATTATCAAAAGCGAAAGTAATAATATCTAAAAAAAAACT  160

ATTACCTTATAAGAAGCTATTACCTAGATGGCATAAGATCATATACTTTTATTTTTGATTAGACTAGAAATACACTAATAT  240

ATTGTGGACATAGCCAGAC AACGATTAGATGGCATACCTCTCTATAAAAACCACAGCTTGAGATGCTCCAATGGCATCCA  320

AATTCCTCAAGTCAAAAAG ATG ATC AGA TTC TTA GTC CTC TCT TTG CTA ATT CTC ACC CTC TTC
                                MET Ile Arg Phe Leu Val Leu Ser Leu Leu Ile Leu Thr Leu Phe
                                                          -20

Fig. 4

CTA ACA ACT CCT GCT GTG GAG GGC GAT GTT AGC TTC CGT TTA TCA GGT GCA ACA AGC AGT
Leu Thr Thr Pro Ala Val Glu Gly Asp Val Ser Phe Arg Leu Ser Gly Ala Thr Ser Ser
                               |Asp Val Ser Phe Arg Leu Ser Gly Ala Thr Ser Ser
                               -1  1

TCC TAT GGA GTT TTC ATT TCA AAT CTG AGA AAA GCT CTT CCA AAT GAA AGG AAA CTG TAC
Ser Tyr Gly Val Phe Ile Ser Asn Leu Arg Lys Ala Leu Pro Asn Glu Arg Lys Leu Tyr
Ser Tyr Gly Val Phe Ile Ser Asn Leu Arg Lys Ala Leu Pro Asn Glu Arg Lys Leu Tyr
                             20

GAT ATC CCT CTG TTA CGT TCC TCT CTT CCA GGT TCT CAA CGC TAC GCA TTG ATC CAT CTC
Asp Ile Pro Leu Leu Arg Ser Ser Leu Pro Gly Ser Gln Arg Tyr Ala Leu Ile His Leu
Asp Ile Pro Leu Leu Arg Ser Ser Leu Pro Gly Ser Gln Arg Tyr Ala Leu Ile His Leu
                             40

```
                                                                            600
ACA AAT TAC GCC GAT GAA ACC ATT TCA GTG GCC ATA GAC GTA ACG AAC GTC TAT ATT ATG
Thr Asn Tyr Ala Asp Glu Thr Ile Ser Val Ala Ile Asp Val Thr Asn Val Tyr Ile MET
Thr Asn Tyr Ala Asp Glu Thr Ile Ser Val Ala Ile Asp Val Thr Asn Val Tyr Ile Met
    EcoR V                              650
GGA TAT CGC GCT GGC GAT ACA TCC TAT TTT TTC AAC GAG GCT TCT GCA ACA GAA GCT GCA
Gly Tyr Arg Ala Gly Asp Thr Ser Tyr Phe Phe Asn Glu Ala Ser Ala Thr Glu Ala Ala
Gly Tyr Arg Ala Gly Asp Thr Ser Tyr Phe Phe Asn Glu Ala Ser Ala Thr Glu Ala Ala
                        60
                    700
AAA TAT GTA TTC AAA GAC GCT ATG CGA AAA GTT ACG CTT CCA TAT TCT GGC AAT TAC GAA
Lys Tyr Val Phe Lys Asp Ala MET Arg Lys Val Thr Leu Pro Tyr Ser Gly Asn Tyr Glu
Lys Tyr Val Phe Lys Asp Ala Met Arg Lys Val Thr Leu Pro Tyr Ser Gly Asn Tyr Glu
                            80                                      100
                                                                                800
AGG CTT CAA ACT GCT GCG GGC AAA ATA AGG GAA AAT ATT CCG CTT GGA CTC CCA GCT TTG
Arg Leu Gln Thr Ala Ala Gly Lys Ile Arg Glu Asn Ile Pro Leu Gly Leu Pro Ala Leu
Arg Leu Gln Thr Ala Ala Gly Lys Ile Arg Glu Asn Ile Pro Leu Gly Leu Pro Ala Leu
    750                                         120
                                                        850
GAC AGT GCC ATT ACC ACT TTG TTT TAC TAC AAC GCC AAT TCT GCT GCG TCG GCA CTT ATG
Asp Ser Ala Ile Thr Thr Leu Phe Tyr Tyr Asn Ala Asn Ser Ala Ala Ser Ala Leu MET
Asp Ser Ala Ile Thr Thr Leu Phe Tyr Tyr Asn Ala Asn Ser Ala Ala Ser Ala Leu Met
            Sal I                           140
                    900
GTA CTC ATT CAG TCG ACG TCT GAG GCT GCG AGG TAT AAA TTT ATT GAG CAA CAA ATT GGG
Val Leu Ile Gln Ser Thr Ser Glu Ala Ala Arg Tyr Lys Phe Ile Glu Gln Gln Ile Gly
Val Leu Ile Gln Ser Thr Ser Glu Ala Ala Arg Tyr Lys Phe Ile Glu Gln Gln Ile Gly
                                                160
```

Fig. 4 (con't)

```
AAG CGC GTT GAC AAA ACC TTC CTA CCA AGT TTA GCA ATT ATA AGT TTG GAA AAT AGT TGG
Lys Arg Val Asp Lys Thr Phe Leu Pro Ser Leu Ala Ile Ile Ser Leu Glu Asn Ser Trp
Lys Arg Val Asp Lys Thr Phe Leu Pro Ser Leu Ala Ile Ile Ser Leu Glu Asn Ser Trp
                            950                         180

TCT GCT CTC TCC AAG CAA ATT CAG ATA GCG AGT ACT AAT AAT GGA CAG TTT GAA ACT CCT
Ser Ala Leu Ser Lys Gln Ile Gln Ile Ala Ser Thr Asn Asn Gly Gln Phe Glu Thr Pro
Ser Ala Leu Ser Lys Gln Ile Gln Ile Ala Ser Thr Asn Asn Gly Gln Phe Glu Ser Pro
            1000                        200                         1100

GTT GTG CTT ATA AAT GCT CAA AAC CAA CGA GTC ATG ATA ACC AAT GTT GAT GCT GGA GTT
Val Val Leu Ile Asn Ala Gln Asn Gln Arg Val MET Ile Thr Asn Val Asp Ala Gly Val
Val Val Leu Ile Asn Ala Gln Asn Gln Arg Val MET Ile Thr Asn Val Asp Ala Gly Val
1050                                    220                    1150 Nco I

GTA ACC TCC AAC ATC GCG TTG AAT CTG CTG AAT CGA AAC AAT ATG GCA GCC ATG GAT GAC GAT
Val Thr Ser Asn Ile Ala Leu Asn Leu Leu Asn Arg Asn Asn MET Ala Ala MET Asp Asp Asp
Val Thr Ser Asn Ile Ala Leu Asn Leu Leu Asn Arg Asn Asn Met Ala
                                        240                 247

GTT CCT ATG ACA CAG AGC TTT GGA TGT GGA AGT TAT GCT ATT TAG TGTAACTTCAAGCTACGT
Val Pro MET Thr Gln Ser Phe Gly Cys Gly Ser Tyr Ala Ile TER
                            1200
```

Fig. 4 (con't)

```
                                                          1
TCS-                                              D V S   R L S   
ricA-                    I F P K Q Y         I   N   R T   A     
abrA-                        E   R   I   F T A T   N   V D Q     
BPSI- A A K M A K N V   K     L F T A T   I     V D Q L         
MIRA-                        A   T L E T I A   L D L N 20
TCS-   T S   Y G V   S N   K A   P N E R K D L
ricA-  T V Q S Y T N   R E   V G R   T   A D L V I F
abrA-  E Q S Y K Q T S   R E A T   L   R   T G N     H E I F
BPSI-  S   A D   A L T S     A T   G E N T     R   T G N D P   H E I F
MIRA-  N P T T   L S   I T N   R T   V A D K   T E Q 40
TCS-     Y   L     S   S   G S N   R         A
ricA-  R   D P V     N R   V T G T   Q   I E P N R P     L
abrA-    D   V       D P V T G T   Q   I E P N R P   W   T
BPSI-  S   N E       P V E I   N V P   T   W     T H
MIRA-        C T I Q K I S K T F P T     R       S Y 60
TCS-     H   T   Y     D   T       S           V
ricA-    P S N H   E   L   V           V
abrA-    L S N S   D         E G       R A D   I
BPSI-    V   A   P T S A G L         R A D   I
MIRA-    D   I V     S   Q K         M A D L 80
TCS-  I M G Y R   G D     T         N E   S A
ricA-    V G Y R   G N   S A       N H P D   N Q S
abrA-    V A   G   T   Q           L E R L D T   N P G
BPSI-  L E   F K S S       G       W W E     T D P     L
MIRA-    L   V S D I A N N K G R A F     K D V T     E 100
TCS-  T E     K     K V     K   A M Q   K V   Y
ricA-  E D   E   I T H       D V Q N   R H Y   F A
abrA-  S     S           D   Q D Y N   R H D   S L
BPSI-  I P G   T   N F       V G   G     D Y N   H   L L
MIRA-  A V   N N F   F P G A     N     I K   T 120
TCS-  S   N   E   Q T A         K I         G
ricA-  G Y N D R     Q T Q A L W   K N       N     N
abrA-  Y   T   G       Q R N   H   S               N
BPSI-    D   I K   T   N W V   L           L D A V
MIRA-  T   S   G         K N     G     K D N       I
```

Fig. 9

Fig. 9 (con't)

RECOMBINANT TRICHOSANTHIN AND CODING SEQUENCE

This is a divisional application of application Ser. No. 333,184, filed Apr. 4, 1989, now abandoned.

FIELD OF THE INVENTION

The present invention relates to recombinantly produced trichosanthin and DNA coding sequences therefore.

REFERENCES

Asano, K., et al., Carlsberg Res Commun, 51:129 (1986).
Barbieri, L., et al., Biochem J, 203:55 (1982).
Bullock, W. O., et al., Biotechniques, 5(4):376 (1987).
Calderwood, S. B., et al., Proc Nat Acad Sci USA, 4364 (1987).
Chaudhary, V. K., et al., Nature, 335:369 (1988).
Coleman, W. H., et al., Biochem Biophys Acta, 696:239 (1982).
Crowe, S., et al., Aids Research and Human Retroviruses, 3(2):135 (1987).
Cumber, J. A., et al., Methods in Enzymology, 112:207 (1985).
Duncan, R. J. S., et al., Anal Biochem, 182:68 (1983).
Falasca, A., et al., Biochem J, 207:505 (1982).
Funatsu, G., et al., Agric Biol Chem, 52(4):1095 (1988).
Gasperi-Campani, et al., FEBS Lett, 76(2):173 (1977).
Grasso, S., et al., Phytopathology, 68:199 (1978).
Gu, Zi-wei, et al., Acta Chemica Sinica, 43:943 (1984).
Halling, K. C., et al., Nuc Acids Res, 13:8019 (1985).
Hsu, K. J., et al., Acta Zool Sin, 22:149 (1976).
Hwang, Y. N., Chinese J Integrated Trad and Western Medicine, 7:154 (1987).
Irvin, J. D., Arch Biochem Biophys, 169:522 (1975).
Kao, H., et al., Acta Biol Exp Sin, 11:253 (1978).
Kuo-Fen, C., et al., Obs and Gyn, 59(4):494 (1982).
Lamb, F. I., et al., Eur J Biochem, 148:265 (1985).
Law, L. K., et al., J Reprod Fert, 69:597 (1983).
Lifson, J. D., et al., Science, 232:1123 (1986).
Lin, J. Y., et al., Toxicon, 16:653 (1978).
Maddon, P. J., et al., Cell, 42:93 (1985).
Maraganore, J. M., et al., J Biol Chem, 262(24):11628 (1987).
Murray, H. G. et al., Nuc Acids Res, 8:4321 (1980).
Ohtsuka, E., et al., J Biol Chem, 260(5):2605 (1985).
Olsnes, S., Nature, 328:474 (1987).
Olsnes, S., et al., in Molecular Action of Toxins and Viruses, (Elsevier, 1982), Chapter 3.
Pan, K., et al., Scientia Sinica (Series B) 30(4):386 (1987).
Spreafico, F., et al., Int J Immunopharmoc, 6(4):335 (1983).
Takahashi, Y., et al., Proc Nat Acad Sci, USA, 82:1931 (1985).
Taylor, B. et al, BRL Focus, 4(3):4 (1982).
Till, M. A., et al., Science, 242:1166 (1987).
Wang, Yu, et al., Pure & Appl Chem, 58(5):789 (1986).
Xiong, Y. Z., et al., Acta Zool Sin, 11:236 (1976).
Xuejan, Z., et al., Nature, 321:477 (1986).
Yeung, H. W. et al., Int J Peptide Protein Res, 27:325 (1986).

BACKGROUND OF THE INVENTION

Trichosanthin (TCS) is a plant protein which is obtained from the Trichosanthes kirilowii root tuber. The protein, which is also known as alpha-trichosanthin (Law) and Radix trichosanthis (Kuo-Fen), is a basic, single-chain protein having a molecular weight of about 25,000 daltons. An incorrect protein sequence of TCS has been reported (Gu; Wang), and a molecular model has been derived from X-ray analysis (Pan).

It has been shown that TCS is a potent inhibitor of protein snythesis in a cell-free lysate system (Maraganore). This activity is consistent with the observed homology in amino acid sequence between TCS and the A chain of ricin, a ribosome-inactivating protein (RIP) which shows amino acid homology with a number of other RIPs, including abrin A chain (Olnes, 1982, 1987) and modeccin (Olsnes, 1982), and various single-chain ribosome-inactivating proteins, such as pokeweed antiviral protein (PAP) (Irvin), RIPs from a variety of other plants (Coleman; Grasso; Gasperi-Campani) and the A subunit of Shiga-like toxins from E. Coli (Calderwood).

TCS, or plant extracts containing TCS, have been used in China as an abortifacient agent in humans, particularly during midtrimester (14 to 26 weeks). As such, the drug has been administered by intramuscular, intravenous, or intraamniotic routes, typically at a single dose of between about 5-12 mg. The phenomenon of mid-term abortion has been attributed to the selective destruction of placental villi. Other studies indicate that the syncytiotrophoblast is preferentially affected (Hsu; Kao) and that secretion of hCG may be impaired (Xiong). TCS has also been shown to have a suppressive effect on human choriocarcinoma, and the protein appears to be able to pass the blood/brain barrier (Hwang).

It has recently been shown that TCS has a selective inhibitory effect on viral expression in human T cells and macrophages infected with human immunodeficiency virus (HIV). This is evidenced by nearly complete inhibition of HIV-derived antigen in infected cells treated with the protein, as well as selective inhibition of protein and DNA synthesis in the infected cells. Similar results were also discovered for momorcharin, a basic glycoprotein obtained from the seeds of the bitter melon plant (Falosia; Spreafico; Lin; Barbieri). These findings, and applications of the two proteins for the treatment of HIV infection, are detailed in U.S. Pat. No. 4,795,739 for "Method of Selectively Inhibiting HIV".

Particularly in view of the ability of TCS to inhibit viral expression in HIV-infected human T cells and macrophages, it would be desirable to produce a relatively pure, invariant preparation of TCS, for use as a human therapeutic agent. Methods of preparing TCS from the roots of T. kirilowii have been reported (Yueng). Analysis of the purified TCS produced by earlier-disclosed known methods indicates that the protein is only partially purified, and in particular, contains hemagglutinating contaminant protein(s). A more recent purification method described in co-owned patent application for "Method of Purifying Trichosanthin", filed on even date herewith, yields a highly purified TCS preparation which is substantially free of protein contaminants, including hemagglutinating proteins.

Additionally, it would be desirable to produce TCS by means of recombinant DNA technology. Synthesis of the protein by recombinant methods would avoid the difficulty of obtaining T. kirilowii roots in fresh form, since at present the tuber roots are available only from certain regions of the Orient. Recombinant production of TCS would also avoid the problem of variations in primary amino acid sequence in TCS obtained from natural root material from different geographic areas.

Recombinant production of TCS would also facilitate the production of peptide derivatives of TCS, including bioactive peptide portions of TCS, and bioactive portions of the protein fused with functional peptides which confer, for example, enhanced target-cell specificity.

SUMMARY OF THE INVENTION

It is therefore one object of the present invention to provide a recombinant TCS protein capable of selectively inhibiting viral expression in HIV-infected human T cells or macrophages.

It is a related object of the invention to provide the coding sequence for TCS from *T. kirilowii*.

Still another object of the invention is to provide sets of degenerate primers corresponding to spaced amino acid regions of TCS which are homologous to spaced amino acid regions of RIPs, for use in selectively amplifying plant-derived genomic sequences which code for such RIPs.

In one aspect, the invention includes a cloned nucleic acid molecule which encodes a trichosanthin protein having the functional properties of Trichosanthes-obtained trichosanthin. The nucleic acid molecule is included in the sequence:

(d) a TCS coding sequence joined with a ligand peptide coding sequence, encoding a fused protein having a ligand peptide which confers cell-surface recognition properties on the fused protein.

The invention also includes the coding sequence for TCS from *T. kirilowii* in combination with an expression vector. One preferred expression vector construction contains a promoter, a ribosome binding site, an ATG start codon positioned adjacent the amino-terminal codon of TCS, and a stop codon positioned adjacent the carboxy terminal codon of mature TCS.

In another aspect, the invention includes a primer mixture for use in selectively amplifying a genomic fragment coding for first and second spaced regions of TCS from *T. kirilowii*, by repeated primer-initiated strand extension. The primer mixture includes a first set of sense-strand degenerate primers, and a second set of anti-sense primers, where each set contains substantially all of the possible coding sequences corresponding to the first and second region of known trichosanthin amino acid sequence, respectively. That is, each degenerate primer set includes at least one primer species which is effective to hybridize with the coding sequence of the corresponding amino acid region.

In a preferred embodiment, the primers in the first and second primer sets are designed to hybridize to first and second coding regions, respectively, which encode

```
    EcoRI
1    GAATTCAAATATTTTCTGAATAAATATAAAATTCATTGTAGAGAAATGATGAGAA           55
56   AACAAGAACAATTTTCAAAAACAAAAAATAAAAAACAAATGGTTTATCAAAGAAG          110
111  GCCCGAATTTATTATCAAAAGGCCGAAAGTTAATAATATCTAGGGAAAAACTATT          165
166  ACCTTATAAGAAGCTATTACCTAGATGGCATAAGATCATACTTTTATTTTTGATT          220
221  TAGACTAGAAATACACTAATATATTGTGGACATAGCCAGACAACGATTAGATGGC          275
276  ATACCTCTCTATAAAAACCACAGCTTGAGATGCTCCAATGGCATCCAAATTCCTC          330
331  AAGTCAAAAAG ATG ATC AGA TTC TTA GTC CTC TCT TTG CTA ATT           374
375  CTC ACC CTC TTC CTA ACA ACT CCT GCT GTG GAG GGC GAT GTT           416
417  AGC TTC CGT TTA TCA GGT GCA ACA AGC AGT TCC TAT GGA GTT           458
459  TTC ATT TCA AAT CTG AGA AAA GCT CTT CCA AAT GAA AGG AAA           500
501  CTG TAC GAT ATC CCT CTG TTA CGT TCC TCT CTT CCA GGT TCT           542
543  CAA CGC TAC GCA TTG ATC CAT CTC ACA AAT TAC GCC GAT GAA           584
585  ACC ATT TCA GTG GCC ATA GAC GTA ACG AAC GTC TAT ATT ATG           626
627  GGA TAT CGC GCT GGC GAT ACA TCC TAT TTT TTC AAC GAG GCT           668
669  TCT GCA ACA GAA GCT GCA AAA TAT GTA TTC AAA GAC GCT ATG           710
711  CGA AAA GTT ACG CTT CCA TAT TCT GGC AAT TAC GAA AGG CTT           752
753  CAA ACT GCT GCG GGC AAA ATA AGG GAA AAT ATT CCG CTT GGA           794
795  CTC CCA GCT TTG GAC AGT GCC ATT ACC ACT TTG TTT TAC TAC           836
837  AAC GCC AAT TCT GCT GCG TCG GCA CTT ATG GTA CTC ATT CAG           878
879  TCG ACG TCT GAG GCT GCG AGG TAT AAA TTT ATT GAG CAA CAA           920
921  ATT GGG AAG CGC GTT GAC AAA ACC TTC CTA CCA AGT TTA GCA           962
963  ATT ATA AGT TTG GAA AAT AGT TGG TCT GCT CTC TCC AAG CAA          1004
1005 ATT CAG ATA GCG AGT ACT AAT AAT GGA CAG TTT GAA ACT CCT          1046
1047 GTT GTG CTT ATA AAT GCT CAA AAC CAA CGA GTC ATG ATA ACC          1088
1089 AAT GTT GAT GCT GGA GTT GTA ACC TCC AAC ATC GCG TTG CTG          1130
1131 CTG AAT CGA AAC AAT ATG GCA GCC ATG GAT GAC GAT GTT CCT          1172
1173 ATG ACA CAG AGC TTT GGA TGT GGA AGT TAT GCT ATT TAG TGT          1214
1215 AAC TTC AAG CTA CGT                                              1229
``` where basepairs 411 to 1151 encode the mature form of TCS isolated from *Trichosanthes kirilowii*.

The nucleic acid of the invention may include:

(a) basepairs 411 to 1151 which encodes mature TCS from *T. kirilowii*;

(b) in addition to (a), basepairs 342–410, which encodes an amino terminal extension of the mature form of TCS from *T. kirilowii*;

(c) in addition to (a), basepairs 1152 to 1208 which encodes a carboxy terminal extension of the mature form of TCS from *T. kirilowii*; and TCS amino acid sequences that are homologous in amino acid sequences to first and second amino-acid sequences in a variety of RIPs, such as ricin A chain, abrin A chain, pokeweed antiviral protein, and barley ribosome inhibitor. The two primer sets may be used to obtain genomic coding sequences for the corresponding RIPs, by repeated primer-initiated strand extension.

Also forming a part of the invention is a recombinant trichosanthin protein having the functional properties of mature trichosanthin (a) derived from *T. kirilowii* and (b) having the sequence:

| Asp | Val | Ser | Phe | Arg | Leu | Ser | Gly | Ala | Thr | Ser | Ser | Ser | Tyr | Gly | Val |
|---|---|---|---|---|---|---|---|---|---|---|---|---|---|---|---|
| Phe | Ile | Ser | Asn | Leu | Arg | Lys | Ala | Leu | Pro | Asn | Glu | Arg | Lys | Leu | Tyr |
| Asp | Ile | Pro | Leu | Leu | Arg | Ser | Ser | Leu | Pro | Gly | Ser | Gln | Arg | Tyr | Ala |

-continued

| | | | | | | | | | | | | | | |
|---|---|---|---|---|---|---|---|---|---|---|---|---|---|---|
| Leu | Ile | His | Leu | Thr | Asn | Tyr | Ala | Asp | Glu | Thr | Ile | Ser | Val | Ala | Ile |
| Asp | Val | Thr | Asn | Val | Tyr | Ile | Met | Gly | Tyr | Arg | Ala | Gly | Asp | Thr | Ser |
| Tyr | Phe | Phe | Asn | Glu | Ala | Ser | Ala | Thr | Glu | Ala | Ala | Lys | Tyr | Val | Phe |
| Lys | Asp | Ala | Met | Arg | Lys | Val | Thr | Leu | Pro | Tyr | Ser | Gly | Asn | Tyr | Glu |
| Arg | Leu | Gln | Thr | Ala | Ala | Gly | Lys | Ile | Arg | Glu | Asn | Ile | Pro | Leu | Gly |
| Leu | Pro | Ala | Leu | Asp | Ser | Ala | Ile | Thr | Thr | Leu | Phe | Tyr | Tyr | Asn | Ala |
| Asn | Ser | Ala | Ala | Ser | Ala | Leu | Met | Val | Leu | Ile | Gln | Ser | Thr | Ser | Glu |
| Ala | Ala | Arg | Tyr | Lys | Phe | Ile | Glu | Gln | Gln | Ile | Gly | Lys | Arg | Val | Asp |
| Lys | Thr | Phe | Leu | Pro | Ser | Leu | Ala | Ile | Ile | Ser | Leu | Glu | Asn | Ser | Trp |
| Ser | Ala | Leu | Ser | Lys | Gln | Ile | Gln | Ile | Ala | Ser | Thr | Asn | Asn | Gly | Gln |
| Phe | Glu | Thr | Pro | Val | Val | Leu | Ile | Asn | Ala | Gln | Asn | Gln | Arg | Val | Met |
| Ile | Thr | Asn | Val | Asp | Ala | Gly | Val | Val | Thr | Ser | Asn | Ile | Ala | Leu | Leu |
| Leu | Asn | Arg | Asn | Asn | Met | Ala | | | | | | | | | |

The recombinant TCS protein may further include an amino-terminal extension having the sequence:

MET Ile Arg Phe Leu Val Leu Ser Leu Leu Ile Leu Thr Leu Phe Leu Thr Thr Pro Ala Val Glu Gly;

and/or a carboxy-terminal extension having the sequence:

Ala Met Asp Asp Asp Val Pro MET Thr Gln Ser Phe Gly Cys Gly Ser Tyr Ala Ile.

The invention further includes a recombinant process for the production of a trichosanthin protein having the functional properties of Trichosanthes-obtained TCS. This recombinant process involves inserting a DNA sequence encoding the TCS protein into an expression vector, transforming a suitable host with the vector, and isolating the recombinant protein expressed by the vector.

These and other objects and features of the invention will become more fully apparent when the following detailed description of the invention is read in conjunction with the accompanying drawings.

BRIEF DESCRIPTION OF THE DRAWINGS

FIG. 1 shows the amino acid sequence of mature TCS isolated from *T. kirilowii* as determined herein (upper line) and as reported previously (lower line);

FIGS. 3A and 3B show the DNA sequence from an amplified genomic fragment containing a portion of the TCS coding sequence, and the corresponding amino acid sequences in the three possible reading frames in both directions;

FIG. 4 shows the nucleotide sequence of the TCS coding region from *T. kirilowii* and adjacent 5'- and 3'-end sequences;

FIG. 9 compares the amino acid sequence of TCS with those of exemplary RIPs.

DETAILED DESCRIPTION OF THE INVENTION

I. Definitions

The terms below have the following meanings as used herein:

A "trichosanthin protein" is a protein having at least about 90% amino acid sequence identity with alphatrichosanthin obtained from *T. kirilowwii*.

A trichosanthin protein has the functional properties of Trichosanthes-obtained trichosanthin if it has (a) the ability to selectively inhibit expression of HIV-antigen in HIV-infected T-cells or monocyte/macrophages, and/or (b) protein-synthesis-inhibitory activity.

II. Producing Recombinant TCS

This section describes methods for obtaining a genomic region containing the coding sequence for TCS from *T. kirilowii*, and for expressing mature TCS protein in a bacterial expression system.

A. TCS Amino Acid Sequence

TCS was purified by a novel method which is detailed in co-owned patent application for "Purified Trichosanthin and Method of Purification", filed on even date herewith, and outlined in Example 1. The protein was at least about 98% pure as judged by HPLC and gel electrophoresis analysis.

The primary amino acid sequence of the purified trichosanthin was determined under contract with the Protein Chemistry Services at Yale University School of Medicine. The sequence is shown in FIG. 1 (upper line) along with the previously published sequence (lower line) of TCS (Gu; Wang). Variations between the two sequences are noted by double underlining.

As seen from FIG. 1, the present sequence differs substantially from the published sequence. Most significant, as compared to the published sequence, the present TCS sequence lacks a block of 10 amino acids at position number 70 and contains an additional sequence of 21 amino acids at position number 222. The present sequence agrees closely with X-ray diffraction data on crystalized TCS, and resolves inconsistancies between X-ray diffraction data and the previously published TCS sequence. The new sequence, particularly including the 21-amino acid addition, also provides greater sequence homology with a number of RIPS, such as ricin A chain and abrin A chain (see below) than the earlier published sequence.

B. TCS Coding Sequence

Figure 2:
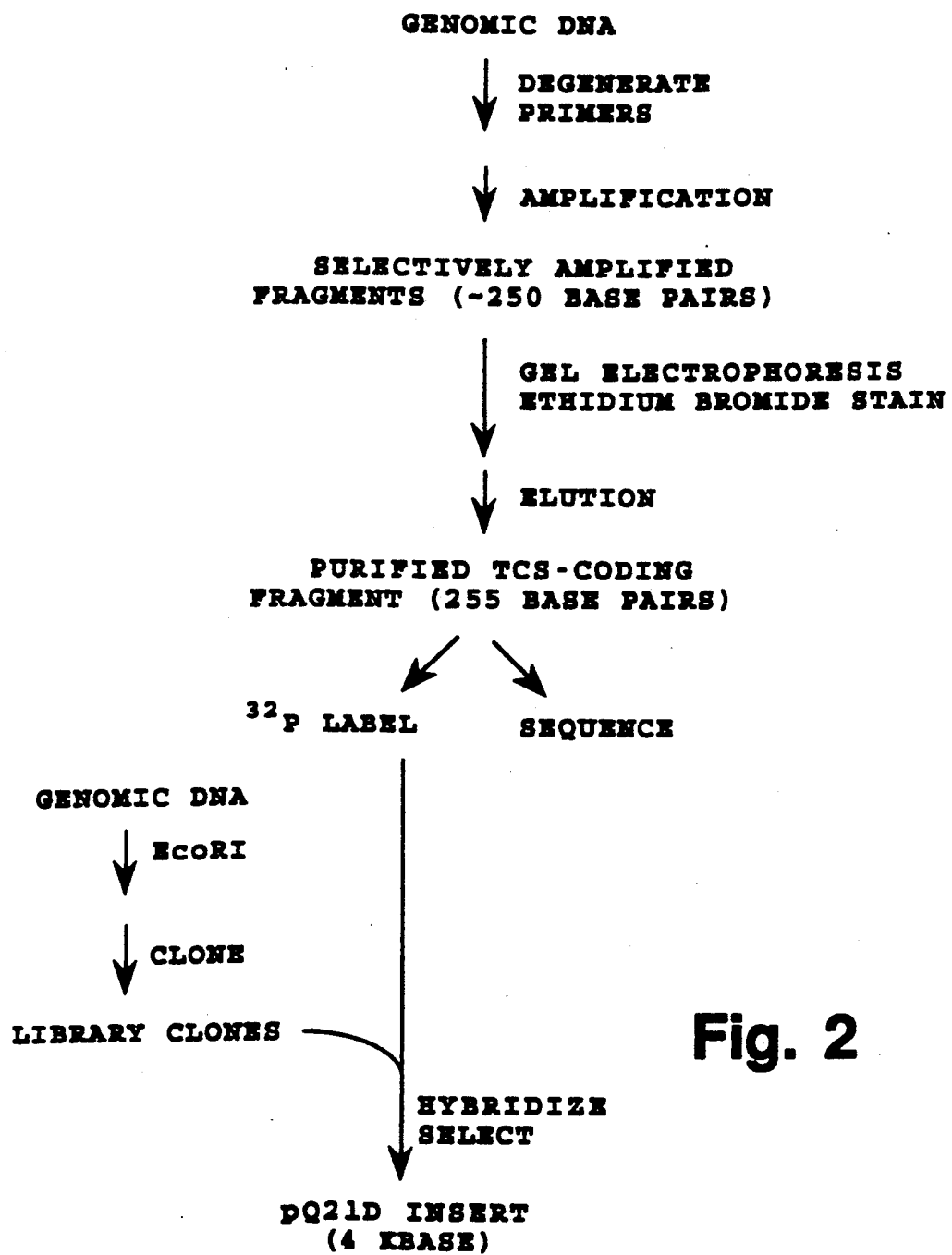
FIG. 2 illustrates the steps in the method used to obtain cloned TCS coding sequences.

FIG. 2 outlines the steps described below for obtaining the complete coding sequence of TCS from *T. kirilowii*. The actual procedure used is given in Example 2.

With reference to the figure, genomic DNA isolated from *T. kirilowii* is mixed with at least two sets of degenerate primers in a reaction mixture designed for carrying out selective amplification of a TCS coding sequence.

In preparing the sets of degenerate primers, two spaced amino acid regions of TCS were selected for coding sequence targeting. The two amino acid sequences which were selected are overlined in FIG. 1 and relate to a 35-mer degenerate primer for the sequence denoted A and to a 32-mer degenerate primer for the sequence denoted B.

Each set of degenerate primers were designed such that at at least one primer sequence is effective to hybridize with the DNA sequence coding for the corresponding amino acid sequence. Deoxyinosine nucleotides were incorporated in order to generate probes longer than 20 nucleotides of manageable complexity (Ohtsuka; Takahashi). One of the two primer sets is designed for hybridization with the anti-sense strand of one coding region, and the other primer set, for hybridization with the sense strand of the second coding region.

The primer set corresponding to the 35-mer includes 128 isomers and is of the general sequence:

5'-GA(A,G)GCIGCIAA(A,G)TA(C,T)GTITT(C,T)AA(A,G)GA(C,T)GCIATG(A,C)G -3' where bases placed in parantheses indicate a mixture and I is inosine. This set is designated MPQP-1, and was designed for binding to the anti-sense strand of the TCS coding region. The other two primer sets, designated MPQP-2 and MPQP-3, each consist of 128 isomers and together comprise all potential coding sequences of the 32-mer and are of the general sequences:

5'- CG(C,T)TTICCIAT(C,T)TG(C,T)TG(C,T)TCIAT(A,G)AA(C,T)TT(A,G)TA -3'     and
5'- CT(C,T)TTICCIAT(C,T)TG(C,T)TG(C,T)TCIAT(A,G)AA(C,T)TT(A,G)TA -3', respectively. They were designed for binding to the sense strand of the TCS coding region, and were typically used in a primer mixture designed MPQP-2/-3.

A DNA amplification reaction was carried out by repeated primer initated strand extension, using a commercially supplied kit (Perkin-Elmer/Cetus) and according to methods supplied by the manufacturer as outlined in Example 2. The product of the DNA amplification step was isolated by agarose gel electrophoresis, and by polyacrylamide gel electrophoresis, with detection by ethidium bromide fluorescence and/or autoradiography. A major product of about 255 base pairs was detected.

FIGS. 3A and 3B show the DNA sequence of the amplified material, and the amino acid sequences corresponding to all three reading frames in both directions. The underlined translation shows a sequence that is homolgous to amino acids 128 through 163 in TCS. This sequence is within the region predicted to be amplified and confirmed that a TCS or TCS-like coding region was amplified.

Southern blot analyses were performed on the DNA prepared from the plant tissue to assess the organization and the complexity of TCS genes in the total DNA background. The Southern blots were probed separately with $^{32}$P-labelled MPQP-1 and MPQP-2/-3. The results (not shown) suggested that there might be several TCS-related genes, and that the overall complexity of the plant genome is on the order of a mammalian genome and could be effectively screened using standard lambda-phage banks.

With continued reference to the method outlined in FIG. 2, the amplified coding sequence from above was used as a probe to identify one or more *T. kirilowii* genomic library clones containing TCS coding sequ According to one aspect, the invention includes a nucleic acid which encodes for a trichosanthin protein which has the functional properties of Trichosanthes-obtained TCS. The nucleic acid preferably has the sequence shown in FIG. 4, where basepairs 411-1151 of the sequence code for mature TCS from *T. kirilowii*. The nucleic acid of the invention may include:

(a) basepairs 411 to 1151 which encodes mature trichosanthin from *T. kirilowii*;

(b) in addition to (a), basepairs 342-410, which encodes a putative amino terminal extension of the mature form of trichosanthin from *T. kirilowii*;

(c) in addition to (a), basepairs 1152 to 1208 which encodes a putative carboxy terminal extension of the mature form of trichosanthin from *T. kirilowii*; and (d) a TCS coding sequence joined with a ligand coding sequence, encoding a fused protein having a ligand peptide which confers cell-surface recognition properties on the fused protein.

C. Expressing Recombinant TCS Protein

Figure 5:
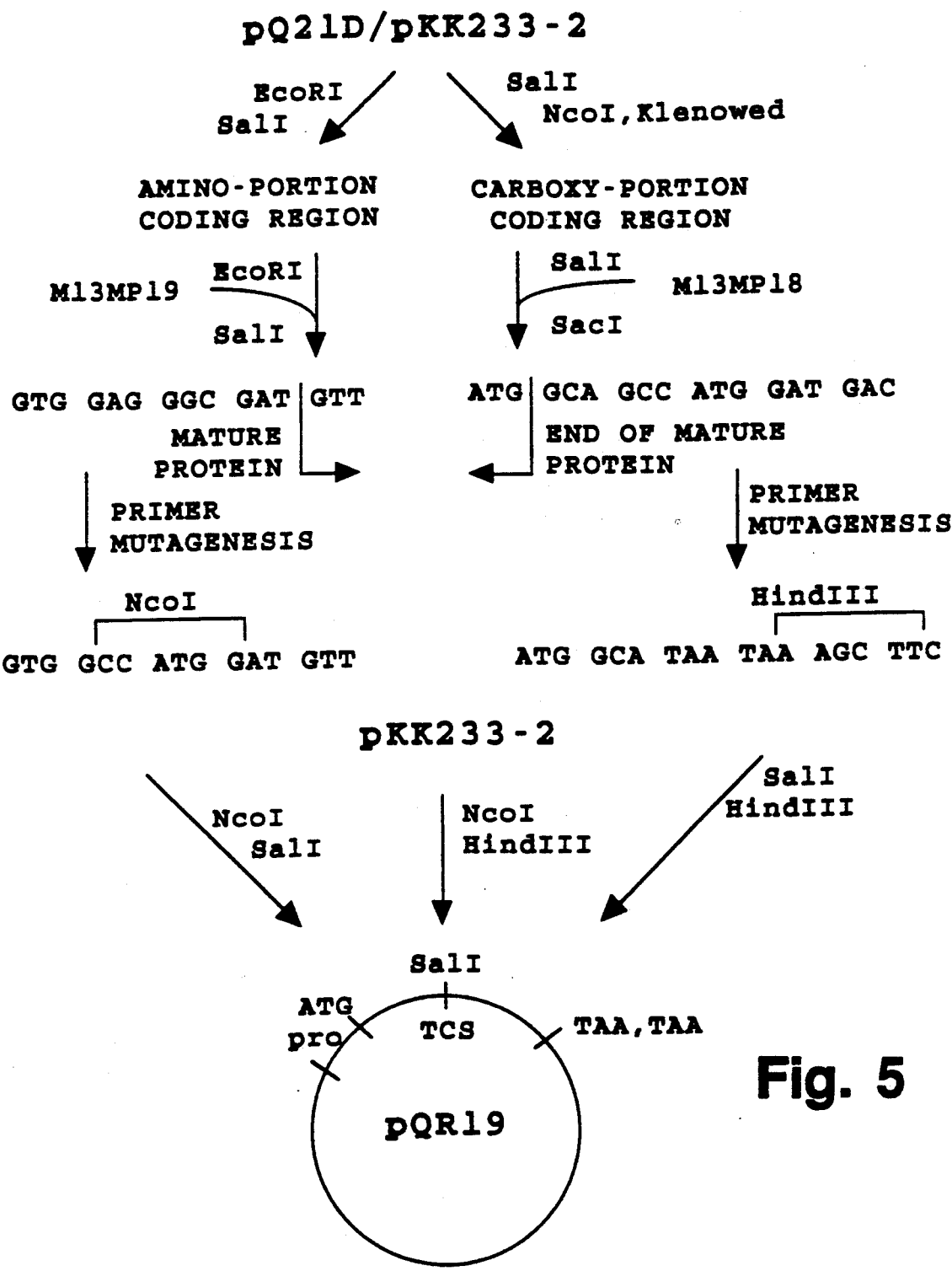
FIG. 5 illustrates the steps in the method used to express mature TCS in a bacterial system.

Recombinant TCS was produced using the above TCS coding sequence, following the steps outlined in FIGS. 4 and 5, and described in Example 5. With reference to FIG. 5, plasmid pQ21D from above was digested with EcoRI and NcoI, releasing a 1.2 kb fragment insert containing the complete coding sequence for TCS. This TCS-coding fragment was cloned into plasmid pKK233-2 which was previously digested with EcoRI and NcoI. After replication the recombinant plasmid, designated pQ21D/pKK233-2, was divided into two samples. One sample was digested with EcoRI and SalI, and and the second sample with SalI and NcoI to generate an EcoRI/SalI amino portion fragment and a SalI/NcoI carboxy portion fragment. The two fragments were cloned into M13 phage vectors for site specific mutagenesis, to place a NcoI site containing an ATG start codon at the amino terminal end of the mature TCS coding sequence, and a double TAA translation stop sequence plus a HindIII cloning site after the carboxy end of the mature sequence, as illustrated in FIG. 5.

The modified sequences were excised, and cloned into a pKK233-2 expression vector (Pharmacia) which contains a synthetic trp/lac promoter positioned appropriately ahead of a ribosome binding site that is also positioned appropriately ahead of an ATG start codon contained within an NcoI site. Several clones were characterized and verified to contain the modified insert in the correct orientation. The DNA sequences of the modified regions were directly verified for one clone, designated pQR19.

More generally, the pQR19 expression vector is exemplary of a TCS coding sequence operatively placed in an expression vector for TCS expression in a suitable host. In a preferred embodiment, and as exemplified by pQR19, the expression vector construction contains a promoter, a ribosome binding site, and an ATG start codon positioned before and adjacent the amino terminal codon of mature TCS, and a stop codon positioned after and adjacent at the carboxy terminal codon of mature TCS.

For expression of recombinant TCS (rTCS), plasmid pQR19 and similar clones were propagated in an appropriate *E. coli* host strain that carries a lacIq gene for regulation of the synthetic trp-lac promoter. The host strain XL-1 Blue (Bullock) was employed. Its relevant genotype is recA1, endA1, gyrA96, thi, hsdR17 (rk-, mk+), supE44, relA1, λ-, lac-[F', proAB, lacIqZΔM15, Tn10 (tet$^R$)]. Induction of promoter activity may be achieved by adding 5 mM IPTG (isopropylthio-galactoside). Under culture conditions described in Example 3, cells carrying pQR19 and similar plasmids were induced and, at a selected cell density, the cells were harvested and disrupted by sonication. Aliquots of total cell material, of material pelleted at 15,000×g for 5 min, and of material remaining in solution at 15,000×g for 5 min were analyzed by polyacrylamide gel electrophoresis and subsequently by Western blot analysis. The Western blot was probed with rabbit anti-TCS sera.

The results showed an immunoreactive product that comigrated with authentic TCS in the total cell and soluble cell fractions from pQR19/XL1-blue induced cells, but not in the insoluble fraction from the same cells, nor in any fraction from pKK233-2(vector)/XL1-blue induced cells, i.e., cells containing the pKK233 expression vector without the TCS coding insert.

The pQR19 expression vector which contains the TCS coding sequence, and which expresses rTCS in a suitable bacterial host has been deposited with The American Type Culture Collection and is identified by ATCC No. 67908.

Clarified cell extract material was fractionated using the steps described in Example 1, yielding rTCS with a purity, as judged by gel band staining with Coomassie blue on SDS polyacrylamide gels, of greater than 90%. About 70 mg of purified rTCS were obtained from nine liters of culture.

The rTCS protein produced is exemplary of an rTCS protein derived from the amino acid sequence shown in FIG. 4. More generally, the rTCS protein of the invention includes a recombinant protein containing the entire amino acid sequence for mature TCS, as described above, and a recombinant TCS protein containing an amino-terminal extension having the sequence:

MET Ile Arg Phe Leu Val Leu Ser Leu Leu Ile Leu Thr Leu Phe Leu Thr Thr Pro Ala Val Glu Gly;

and/or a carboxy-terminal extension having the sequence:

Ala MET Asp Asp Asp Val Pro MET Thr Gln Ser Phe Gly Cys Gly Ser Tyr Ala Ile.

The invention thus further includes a recombinant process for the production of a trichosanthin protein having the functional properties of Trichosanthes-obtained trichosanthin. The method includes the steps of inserting a DNA sequence encoding said protein into an expression vector, transforming a suitable host with the vector, and isolating the recombinant protein expressed by the vector.

In one preferred embodiment, the expression vector is pQR19 and the host is *E. coli*.

D. Bioactivity of Recombinant TCS

As previously described in above-cited U.S. Pat. No. 4,795,739, TCS obtained from *T. kirilowii* is a potent and selective inhibitor of HIV antigen expression in HIV-infected T cells and monocyte/macrophages. The inhibitory effect of rTCS on expression of HIV-specific antigens in HIV-infected T cells can be demonstrated as follows: Acutely HIV-infected human T cells were treated with varying concentrations of rTCS. After four days culture, the amount of HIV p24 antigen present in cell free culture supernatants was quantitated using a commercially available antigen capture immunoassay (Coulter). Inhibition was determined by comparison of results for treated cultures and untreated cultures.

Figure 6:
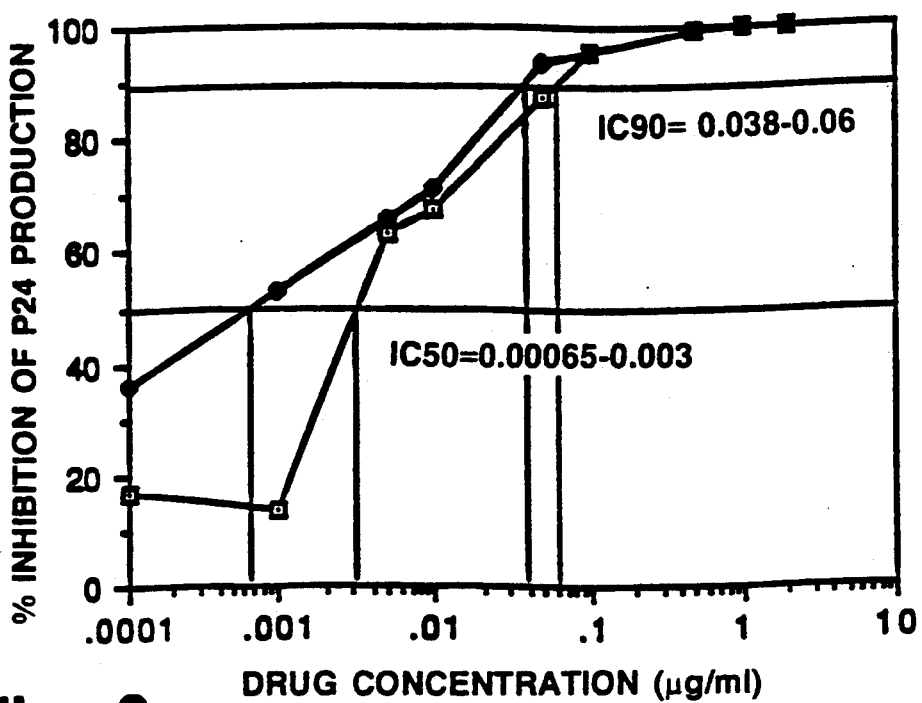
FIG. 6 shows plots of percent inhibition of HIV antigen (p24) production as a function of culture concentration of plant-derived TCS (open-boxes) and rTCS (closed boxes)

The viral inhibition studies detailed in Example 4A compared the inhibitory activity of plant-produced TCS with the above rTCS protein. The plots in FIG. 6 show percent inhibition of p24 HIV antigen production as a function of culture concentration of plant derived TCS (open boxes) and rTCS produced as above (open boxes). As seen, both proteins gave substantially the same level of inhibition at higher protein concentrations, although the plant-derived protein was more effective at the lowest protein concentrations.

Figure 7:
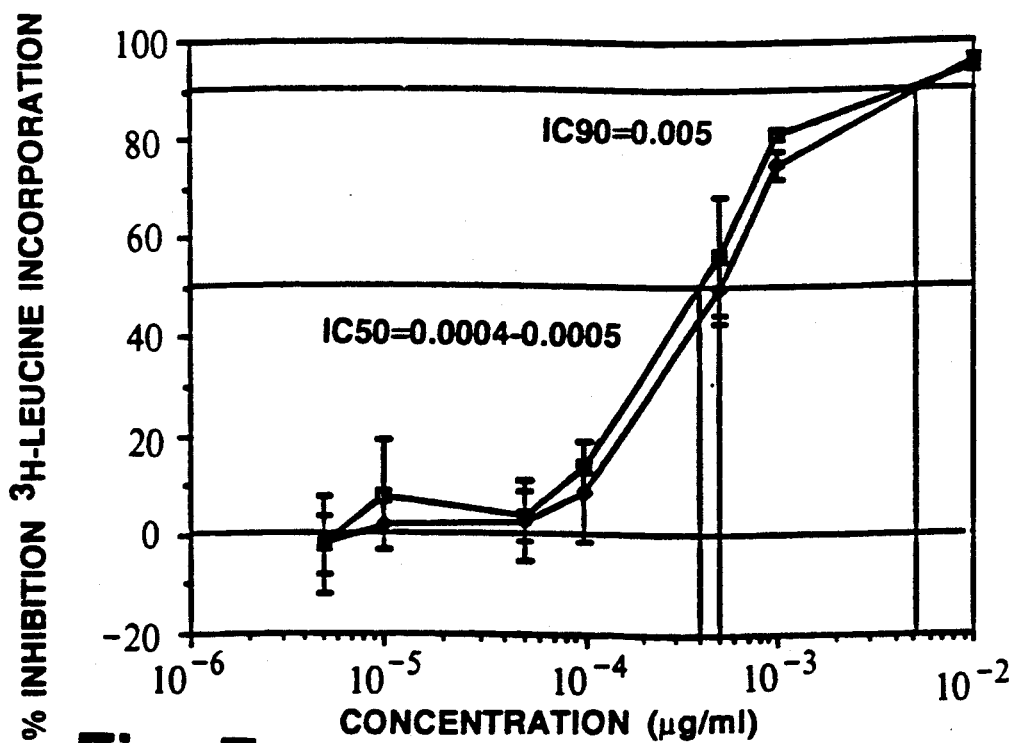
FIG. 7 shows plots of percent inhibition of $^3$H-leucine incorporation into trichloroacetic acid precipitable protein as a function of concentration of plant derived TCS (open boxes) and rTCS (closed boxes) in a cell free rabbit reticulocyte lysate protein synthesizing system.

Also, as mentioned above, it has been shown that plant-produced TCS is a potent inhibitor of protein synthesis in a cell-free lysate system. The protein-synthesis inhibitory properties of both plant-produced TCS and rTCS were compared in a reticulocyte lysate system, as outlined in Example 4B. The plots in FIG. 7 show percent inhibition of $^3$H-leucine incorporation as a function of concentration of plant-derived TCS (open boxes) and rTCS (closed boxes) in the reticulocyte system. The plots show that both plant-produced and recombinant TCS have substantially the same specific protein synthesis inhibitory activity.

E. TCS Fusion Protein

In another aspect, the invention includes TCS fused at its amino or carboxy end with a ligand peptide to form a fused ligand/TCS protein. The TCS making up the fused protein is preferably rTCS or bioactive portion thereof, as described above.

Where TCS is used to inhibit viral expression in HIV-infected human cells, the protein may be advantageously fused with a soluble CD4 peptide, which shows specific binding to the HIV-related gp120 antigen present on the surface of HIV-infected cells (Ti11), or with a monoclonal antibody specific against an HIV-specific cell surface antigen.

The fused TCS protein may be formed by chemical conjugation or by recombinant techniques. In the former method, the peptide and TCS are modified by conventional coupling agents for covalent attachment. In one exemplary method for coupling soluble CD4 to TCS, recombinant CD4 (rCD4) is derivatized with N-succinimidyl-S-acetyl thioacetate (Duncan), yielding thiolated rCD4. The activated CD4 compound is then reacted with TCS derivatized with N-succinimidyl 3-(2-pyridyldithio) propionate (Cumber), to produce the fused protein joined through a disulfide linkage.

As an alternative method, recombinant TCS (rTCS) may be prepared with a cysteine residue to allow disulfide coupling of the rTCS to an activated ligand, thus simplifying the coupling reaction. The TCS expression vector used for production of rTCS can be modified for insertion of an internal or a terminal cysteine codon according to standard methods of site-directed mutagenesis.

Figure 8:
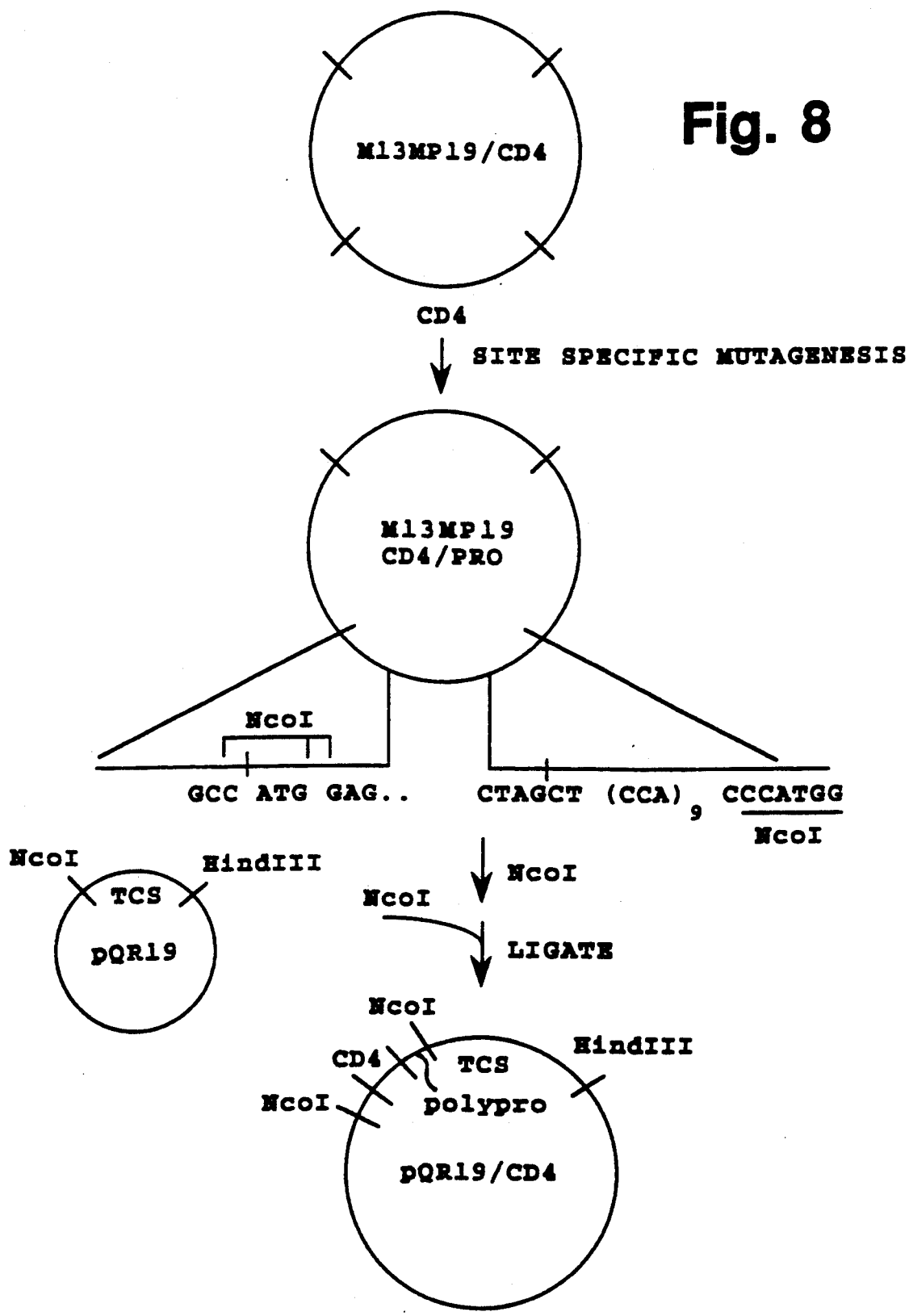
FIG. 8 illustrates the steps in a method for producing a fused TCS protein containing a CD4+ peptide moiety.

In a preferred method, the fused protein is prepared recombinantly using an expression vector in which the coding sequence of the fusion peptide is joined to the TCS coding sequence. FIG. 8 illustrates the construction of an exemplary expression vector for a fused TCS/CD4 protein.

Briefly, an EcoRI-StuI DNA fragment containing the coding region for the first 183 amino acids of mature CD4 peptide (Maddon) is inserted into an M13MP19 phage between SmaI and EcoRI sites and the vector, in a single-strand form, is then subjected to primer mutagenesis. Specifically, the amino-terminal portion of the CD4 gene is modified with primer MP101 (5'- CCAG-CAGCCATGGAGGGAAACAAAG -3'); and the carboxy portion of the gene is modified with primer MP102 (5'-CATCGTGGTGCTAGCTCCACCAC-CACCACCACCACCACCACCACCCATG-GAGGC ATGCAAGCTTG -3'). These modifications place an NcoI site containing an ATG start codon at the beginning of the mature CD4 peptide coding sequence, and a string of proline codons terminating at an NcoI cloning site after amino acid 180 in the CD4 sequence, as illustrated in FIG. 8.

The NcoI fragment from the phage vector is inserted into the pQR19 expression vector from above previously cut with NcoI. Successful recombinants are confirmed by restriction analysis for proper orientation of the CD4 sequence insert.

An expression vector formed as above, and designated pQR19/CD4 in FIG. 8, contains (a) a synthetic trp/lac promoter positioned appropriately ahead of a ribosome binding site that is also positioned appropriately ahead of an ATG start codon contained within an NcoI site, (b) the CD4 coding sequence, (c) a spacer coding sequence coding for 10 proline residues, which spaces the CD4 and TCS protein moieties, (d) the coding sequence for mature TCS and (e) a stop codon positioned adjacent the carboxy-terminal codon of mature TCS. The method generally follows that used in fusing a soluble CD4 to domains 2 and 3 of pseudomonas exotoxin A, as described previously (Chaudhary).

Plasmid pQR19/CD4 is analysed for expression of fused TCS protein as above. Briefly, the expression vector is cultured in a suitable bacterial host under IPTG induction conditions to a desired cell density. The cells are harvested, ruptured by sonication, and the cell material is clarified by centrifugation. The clarified material is tested for (a) binding to gp120 antigen, to confirm CD4 ligand binding activity, and (b) for ribosome inhibition activity, to confirm TCS enzymatic activity.

The protein may be purified by molecular-sieve and ion-exchange chromatography methods, with additional purification by polyacrylamide gel electrophoretic separation and/or HPLC chromotography, if necessary.

It will be appreciated from the above how other ligand/TCS-containing fusion proteins may be prepared. One variation on the above fusion is to exchange positions of the CD4 and TCS molecules in the fusion protein.

III. Obtaining RIP Coding Sequences

As described above, the coding sequence of TCS was obtained by selective amplification of a TCS coding region, using sets of degenerate primers for binding to spaced coding regions of a TCS coding sequence in genomic DNA. This section describes the use of such sets of degenerate primers for selective amplification of coding sequences for a variety of RIPs.

In selecting suitable primer sets, the amino acid sequences of TCS and one or more RIPs are examined for regions of sequence homology, i.e., regions where the amino acids sequences are identical or differ at most by one or two amino acid residues. Typically, the length of the regions being examined should contain at least about 7 amino acids, i.e., at least about 20 nucleotides, although it is appreciated that longer oligonucleotide primers are preferred, even though overall complexity is increased.

Figure 9:
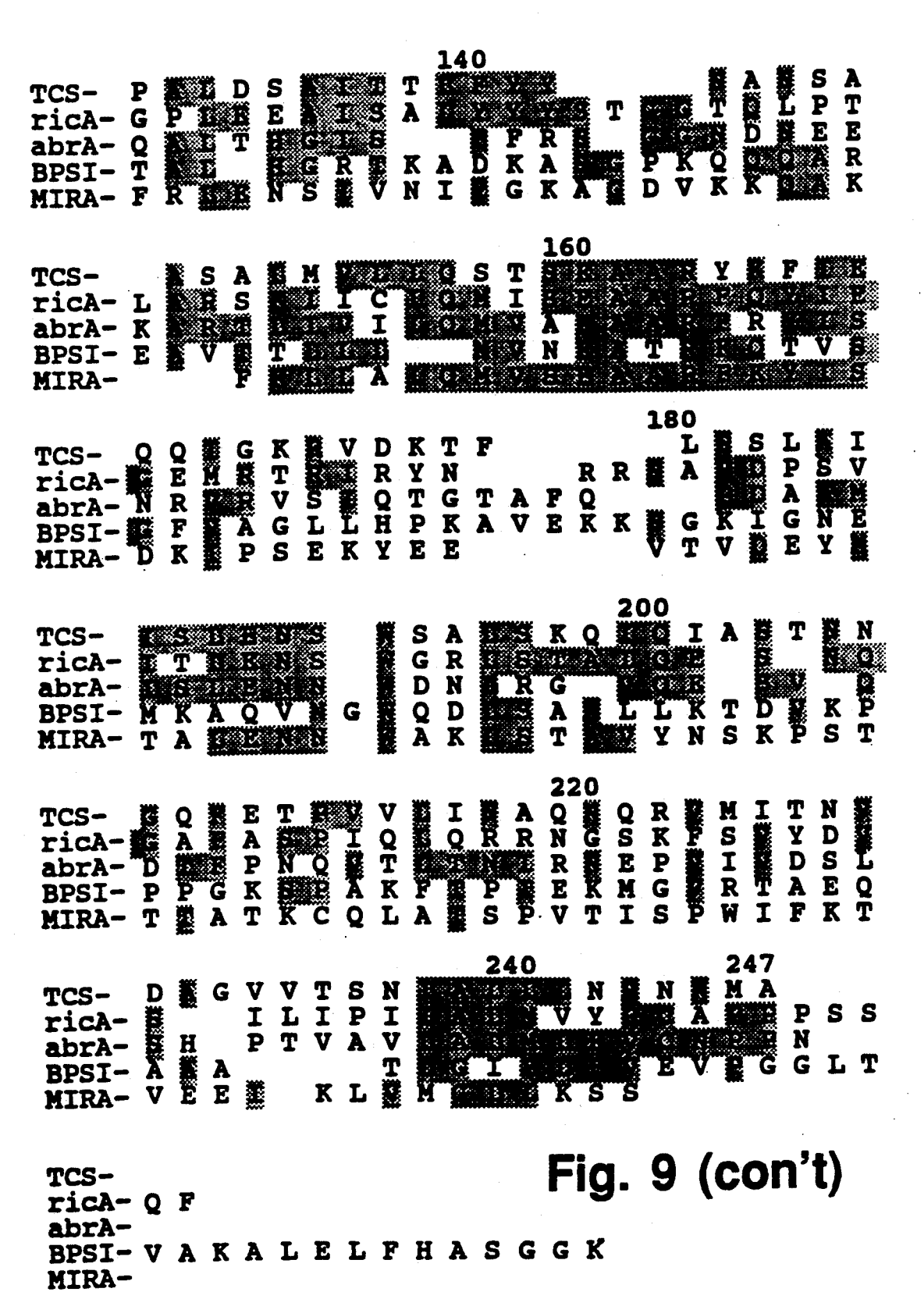

FIG. 9 shows the complete amino acid sequences of TCS (top line), and three RIPs whose sequences have been published. The RIPs are ricin A chain (Lamb), abrin A chain (Funatsu) and barley ribosome inhibitor (Asano). The amino acids are indicated by conventional one-letter codes. Amino acid matches among the four proteins are shaded.

As seen from the figure, there are several regions, each containing at least seven amino acids, which show a high degree of amino acid sequence homology among the proteins, i.e., sequence matching in at least about 4 of the 7 amino acid positions. The relatively greater homology among TCS, ricin A chain and abrin A chain, as compared with barley ribosome inhibitor, presumably reflects evolutionary divergence since TCS, ricin A and abrin A chain are all derived from dicotyledons, and barley inhibitor is obtained from a monocotyledon.

Considering the sequences from amino acids 8–14 in the upper line in FIG. 9, it is seen that the amino acid sequence for abrin A chain —GATSQSY— differs from the corresponding TCS and ricin A chain sequences by only 1 amino acid each, and therefore is a likely choice for design of the primer set. The disadvantage of the GATSQSY sequence is that the presence of two serine residues (S) introduces a six-fold degeneracy at two points in the sequences. However, this problem is not prohibitive if inosine (I) is used in the third and/or first codon position, to reduce degeneracy (down to as little as twofold).

The abrin sequence in the same 8–14 amino acid region differs from the corresponding TCS by a proline-to-serine substitution in the fifth position. Since an ICI sequence will hybridize with both the proline and four of the serine codons, and an additional AGI sequence will hybridize with the other two serine codons, the primers can be made two fold degenerate at this position to encompass both TCS and abrin coding sequences.

Likewise, the abrin sequence in this region differs from the corresponding ricin A chain sequence by a serine-to-valine substitution in the fourth amino acid position. Since an III sequence is needed to bind to both the serine and proline codons, this position can be made completely neutral. The other five amino acid positions are preferably made degenerate, to optimize the specificity of primer binding to corresponding genomic coding regions. The total number of primers in the final primer set is preferably between about 16–128 although more complex mixtures can be used. The primers are synthesized conventionally using commercially available instruments.

A second set of degenerate primers from another region of TCS which is homologous in amino acid sequence to RIPs is similarly constructed.

The two primer sets are useful in a method for selectively amplifying RIP coding sequences present in genomic DNA from selected plant sources, employing repeated primer-initated nucleic acid amplification. As an example, to amplify coding sequences for abrin A chain protein, genomic DNA from *Abrus precatorius* is isolated, and mixed with the primer sets, all four deoxynucleosides triphosphates, and polymerase, as outlined in Example 2. After repeated cycles of primer binding and strand extension, the material is fractionated by gel electrophoresis and amplified fragments are identified, for example, by ethidium bromide staining or by autoradiography, according to procedures described in Example 2. Fragments amplified from an RIP gene can be identified by size, as the selection of specific primer sets would predict the size range of the fragment that is amplified. Genes for RIPs are not believed to contain any introns (Halling and the present application).

The amplified material is then used as a (radiolabeled) probe for detecting genomic library clones prepared from genomic DNA from the plant source, e.g., *Abrus precatorius*. The identified library clones are analysed, as above, for fragments containing a complete RIP coding sequence. Alternatively, overlapping genomic library fragments containing amino and carboxy portions of the coding sequence can be combined to produce a complete coding sequence.

More generally, this aspect of the invention includes a primer mixture and method of using the mixture for selectively amplifying RIP coding sequences. The primer mixture includes a first set of sense-strand degenerate primers, and a second set of anti-sense primers, where each set contains at least one primer sequence which is effective to hybridize with the corresponding coding sequence in TCS which encodes the region of amino acid homology with RIPs, particularly RIPs from dicotyledon plants.

Once the amplified genomic sequence is obtained, as described, the sequence can be used as a probe for isolating genomic library fragments containing the desired RIP coding sequence.

It will be appreciated that the method can be used to obtain the coding sequence from plants which produce known RIPs, and also to screen other plants for the presence of genes encoding as-yet-unknown RIP or RIP-like proteins.

The following examples illustrate various methods used to obtain and verify the nature of the coding sequence and recombinant proteins described above. The examples are intended to illustrate, but in no way to limit, the scope of the invention.

Materials and Methods

*T. kirilowii* root tubers were obtained from the Canton region of the People's Republic of China. Leaves of *T. kirilowii* were obtained from Korea and were collected and immediately frozen on dry ice for shipment. Samples were than stored at −70° C.

QAE Zetaprep TM anion exchange cartridges and SP Zetaprep TM cation exchange cartridges were supplied by AMF Cuno Corp. (Meridan, Conn.); and Pellicon ultrafiltration membranes (10,000 MW cutoff), from Millipore Corp. (Bedford, Mass.).

M13/MP18 and M13/MP19 were obtained from New England Biolabs (Beverly, Mass.). Lambda-Zap II TM cloning vector system was supplied by Stratagene (La Jolla, Calif.). Expression vector PKK233-2 and its IPTG-inducible *E. coli* host strain, XLI-blue, were obtained from Pharmacia (Piscataway, N.J.) and Stratagene (La Jolla, Calif.), respectively. Restriction enzymes were obtained from New England Biolabs (Beverly, Mass.) or Promega (Madison, Wis.). DNA primer-initiated amplification reagents were obtained from Perkin-Elmer/Cetus (Norwalk, Conn.).

Synthetic oligonucleotide primers were prepared by conventional, automated phosphoramidite methods using either a Biosearch Cyclone or an Applied Biosystems Model 380B instrument.

The methods for preparation and manipulation of nucleic acids, and the recombinant DNA techniques emloyed herein are broadly accepted and applied and are generally referenced by Ausubel, F. M. et al. (eds)

"Current Protocols in Molecular Biology" Vols. 1 and 2, John Wiley & Sons, New York (1988) and Maniatis, T., et al., "Molecular Cloning. A Laboratory Manual," Cold Spring Harbor Laboratory, 1982.

EXAMPLE 1

Purification of TCS

A clarified extract of the roots of *T. kirolowii* was obtained by overnight extraction of homogenized tubers of *T. kirilowii*. The extract was clarified by centrifugation, and the clarified material was passed through a QAE Zetaprep TM anion exchange resin, which is supplied commercially in cartridge form. The ion exchange step was carried out at low ionic strength, i.e., low conductivity, which has been found effective to enhance TCS purification, and in particular, to remove hemagglutinin contaminants. The low-conductivity buffer was 20 mM phosphate, pH 8.0.

The flowthrough from the anion exchange resin was adjusted in pH and ionic strength, and preferably concentrated, preparatory to further protein purification by chromatography on a cation exchange resin. The concentration step was carried out by ultrafiltration using a 10,000 molecular weight filtration membrane, yielding a solution which is largely free of low-molecular weight contaminants.

The treated flowthrough material equilibrated with 50 mM phosphate, pH 8.0 buffer was applied to an equilibrated SP Zetaprep TM cation exchange resin, and the column was washed extensively with buffer (15–20 volumes) until the elution profile reached a baseline value. The extensive washing removed loosely bound material, including, particularly, endotoxins and high molecular weight lipopolysaccharides (LPS), and is necessary for achieving high purity TCS.

TCS was now eluted from the column in highly purified form by elution with 50 mM phosphate buffer, pH 6.0 containing 60 mM NaCl, to release bound TCS from the resin. The purified TCS protein was at least about 98% pure, as evidenced by HPLC profile and staining patterns on SDS gel electrophoresis.

EXAMPLE 2

Preparing Cloned Genomic Fragment Containing TCS Coding Sequence

A. Amplified TCS Coding Sequence

Genomic DNA was isolated from frozen *T. kirilowii* leaves by a modification of published methods (Taylor). Briefly, frozen tissue was ground to a fine powder using a mortar and pestle kept on dry ice. β-mercaptoethanol was then added to 2% of the initial volume followed by an equal volume of hot 2× extraction buffer (2% cetyl-trimethyl-ammonium bromide (CTAB), 100 mM Tris-Cl, pH 8.0, 20 mM EDTA, 1.4M NaCl).

This slurry was gently stirred in a 55° C water bath until the temperature reached 50° C. The slurry was then transferred to appropriate centrifuge bottles and extracted twice with an equal volume of chloroform-:isoamyl alcohol (24:1). Phase separation was achieved by centrifugation. A 1/10 volume of 10% CTAB was added and the extraction repeated.

The upper aqueous phase was removed to another container and the DNA precipitated by adding an equal volume of precipitation buffer (1% CTAB, 50 mM Tris-Cl, pH 8.0, 10 mM EDTA) to lower the sodium concentration to 0.35M. The DNA was collected and washed with cold 70% ethanol, 0.1M sodium acetate to convert the DNA to a sodium salt, followed by a wash by 95% cold ethanol. The DNA could then be dried and redissolved in 10 mM Tris-Cl, pH 7.5, 1mM EDTA. To further eliminate contaminants, the DNA was re-precipitated from CTAB by adding an equal volume (original) of 2× extraction buffer, followed by two volumes of (original) TE buffer (10 mM Tris-HCl, 1 mM EDTA), pH 8.0. The DNA was once again converted to the sodium salt, washed with ethanol as above, dried, and dissolved in TE buffer, pH 8.0. Greater than 5 mg of high molecular weight DNA was obtained from approximately 35 g of tissue.

Three degenerate sets of probe sequences were synthesized, corresponding to two separate coding regions. The first DNA sequence is a 35-mer and encompasses the protein sequence overlined and denoted A in FIG. 1, and the second sequence is a 32-mer and encompasses the protein sequence overlined and denoted B in the figure.

The probe sets were prepared by conventional automated methods using instruments commercially available and following the manufacturers, instructions. (Biosearch, San Rafael, Calif., and Applied Biosystems, Foster City, Calif.). Deoxyinosine nucleotides were incorporated in order to generate probes longer than 20 nucleotides of manageable complexity (Ohtsuka; Takahashi). The sense-strand probe set corresponding to the 35-mer, designated MPQP-1, included 128 isomers. The anti-sense-strand second and third sets, designated MPQP-2 and MPQP-3, each included 128 isomers and were 32-mers.

A DNA amplification reaction was carried out by repeated primer initated strand extension, in a reaction mixture containing (a) 1–2 micrograms of the *T. kirilowii* DNA isolated as above, (b) $^{32}$P-labeled [$^{32}$P]MPQP-1 and an equimolar mix of [$^{32}$P]MPQP-2 and -3, as primers, (c) all four deoxynucleoside triphosphates, and (d) Taq polymerase. About 20 rounds of thermal cycling were performed, employing conventional DNA amplification reaction conditions, as outlined in instructions from the manufacturer (Perkin Elmer-Cetus, Norwalk, Conn.). A similar DNA-amplificaticn reaction was carried out using unlabeled primer sets.

The product of the DNA amplification step was fractionated on 3% Nusieve, 1% ME agarose (Seakem TM, FMC Bioproducts, Rockville, Md.) and stained with ethidium bromide. A major product of about 255 base pairs was detected. The material was also fractionated on 5% polyacrylamide gel electrophoresis and the bands detected by autoradiograpy, with similar results. In both cases, very little DNA other than the amplified material was detected.

Amplified DNA was recovered from polyacrylamide gels by elution followed by ethanol precipitation. A portion of one such preparation, approximately 100 nanograms, was taken for DNA sequence analysis. The DNA sample plus 30 ng of unlabeled MPQP-1 were taken up in 10 μl of TE (10mM Tris-Ncl, pH 7.5, 1 mM EDTA) and heated to 100° C for 5 minutes to denature the double-stranded fragment. The mixture was quick frozen on dry ice to prevent the template from annealing. Two μl of 5× Sequenase sequencing buffer (USB Biochemicals, Cleveland, Ohio) was added and the primer allowed to anneal to the template for 5 minutes at 37° C. The standard sequencing protocol supplied by the manufacturer was then followed.

The DNA sequence obtained and its translation into all three reading frames is shown in FIGS. 3A (for the sense strand) and in FIG. 3B (for the complementary strand).

B. Cloned Library Fragment with the Complete TCS Coding Sequence

Genomic DNA obtained as above was digested to completion with EcoRI and cloned into a standard library cloning vector, in this case, the Lambda-Zap II ™ system of Stratagene (La Jolla, Calif.). For use as a probe, the amplified 255-bp fragment from above was radiolabeled by random priming (Boehringer-Mannheim kit, Indianapolis, Ind.).

Approximately $0.5-1.0 \times 10^6$ plaques were probed with the $^{32}$P-radiolabeled 255-bp probe. Two clearly positive plaques were picked, amplified and converted to plasmid, according to protocols supplied by Stratagene. One clone, designated pQ21D, contained an approximate 4 kb insert which included the complete TCS coding sequence.

The region containing the TCS coding region was sequenced by standard double-strand sequence methods, using universal sequence primers as well as unique synthetic oligonucleotide primers as needed. A smaller subclone containing only the TCS coding region was generated by subcloning the 1.2 kb EcoRI to NcoI fragment (FIG. 4) from pQD21D into pKK233-2. The resulting recombinant plasmid was designated pQD12D/pKK233-2.

EXAMPLE 3

Expressing Recombinant TCS (rTCS)

The pQ21D/pKK233-2 cloning vector from Example 2 was divided into two samples. One sample was digested with EcoRI and SalI, to release an EcoRI to SalI fragment containing the amino portion of the TCS gene. A second portion of the DNA was digested first with NcoI, and treated with Klenow to generate a blunt end. The DNA was then digested with SalI to release a SalI to NcoI (blunt) fragment containing the carboxy portion of the gene. After isolating the two fragments by gel electrophoresis, the EcoRI to SalI fragment was cloned into M13MP19 (EcoRI to SalI), and the SalI to NcoI (Klenow repaired) fragment was cloned into M13MP18 (SalI to SmaI). Fragment insertion and production of single-strand phage DNA was performed according to known methods.

The phage single-strand DNA's were subjected to primer mutagenesis using standard methods. The amino portion of the gene (in the M13MP19 vector) was modified with primer QNcoN (5'-CCTGCTGTGGCCATGGATGTTAGC-3'); and the carboxy portion of the gene was modified with primer QTer01 (5'-CGAAACAATATGGCATA ATAAAGCTTCCGAGCTCG-3'). These modifications placed an NcoI site containing an ATG start codon at the beginning of the mature TCS protein sequence and a double TAA translation stop sequence plus a HindIII cloning site after the carboxy end of the mature sequence, as illustrated in FIG. 5.

The modified sequences were excised from purified phage DNA as an NcoI-SalI and an SalI-HindIII fragment, respectively, and cloned together into NcoI-HindIII digested pKK233-2. pKK233-2 is a plasmid containing a synthetic trp/lac promoter positioned appropriately ahead of a ribosome binding site that is also positioned appropriately ahead of an ATG start codon contained within an NcoI site. It is supplied commercially (Pharmacia).

Several clones were characterized and verified to contain the modified insert. The DNA sequences of the modified regions were directly verified for one, designated pQR19.

The plasmid pQR19 and similar clones were propagated in the E. coli host strain, XL1-blue. The significant feature of the strain is that it carries the lacIq repressor gene on a F' episome (discussed above). LacIq protein controls expression from the lac operator and is blocked from repression by the addition of IPTG to 5 mM.

Plasmid pQR19 and another isolate were analyzed for expression of TCS. Cultures were first grown in Luria broth medium supplemented with 100 μg/ml ampicillin, to select for maintenance of the plasmid, to a density of 0.7 measured at 600 nm before adding IPTG, then allowed to grow for 4 hours. These conditions did not result in high levels of expression.

Cultures were then inoculated in Luria broth plus 100 μg/ml ampicillin containing 5 mM IPTG, and allowed to grow to saturation density overnight (pQR19/XL1-blue induced cells). The induced cells were collected by centrifugation, resuspended in 100 mM Tris-HCL, pH 8.5, 5 mM EDTA at a concentration of about 10 $A_{600}$ units/ml and disrupted by sonication. Aliquots were taken and centrifuged at $15,000 \times g$ for 5 minutes to separate soluble from insoluble components.

The insoluble, pelleted material was resuspended in sonication buffer to the same volume as the original aliquot. Samples of each fraction were run on 10% SDS-PAGE. One set of samples was stained for total protein with Coomassie Blue; another set of samples was blotted for Western analysis, with the results discussed in Section II.

EXAMPLE 4

Biological Activity of rTCS A. Inhibition of HIV Replication

The ability of rTCS to mediate selective inhibition of HIV replication in infected T-cells was evaluated in parallel with purified plant-derived material. Cells of the CD4+ T-cell line VB (Lifson, 1986) were inoculated with HIV-1 by incubation at 37° C. for one hour with an aliquot of a titered cryopreserved HIV-1 virus stock (virus isolate HIV-1$_{DV}$ (Crowe, 1987)). After washing, the cells were resuspended to $1.11 \times 10^5$ per ml, and 0.9 ml of this suspension plated in replicate wells of 24 well culture plates. 0.1 ml volumes of serial dilutions of purified plant-derived TCS and rTCS were then added at 10× the desired final concentrations to yield 1.0 ml cultures containing $1 \times 10^5$ cells in 1.0 ml of culture medium containing the desired concentration of TCS. After culturing for 4 days at 37° C. in a humidified 5% CO$_2$/air atmosphere, culture supernatants were harvested and viral replication in treated and control cultures was assessed by measuring HIV p24 antigen content using a commercially available capture immunoassay kit according to manufacturer's instructions (Coulter, Hialeah, Fla.).

As shown in FIG. 6 (open boxes), in accord with observations reported elsewhere (U.S. Pat. No. 4,795,739), plant-derived TCS purified to apparent homogeneity from the root tubers of T. kirilowii inhibited HIV replication in a concentration-dependent fashion in this acute infection assay system. The biological activity of rTCS produced in E. coli and purified to apparent homogeneity (closed boxes), was essentially indistinguishable from that of the native product when tested in parallel in an assay system for inhibition of HIV replication at TCS concentrations above 0.005 μg/ml (FIG. 6). At lower concentrations, rTCS appears to show slightly less specific activity than the plant-derived protein.

B. Inhibition of Cell Free Translation In Vitro

The ability of TCS to irreversibly inactivate ribosomes, thereby inhibiting protein synthesis, is conveniently measured in standardized assays of in vitro translation utilizing partially defined cell free systems composed, for instance, of a reticulocyte lysate preparation as a source of ribosomes and various essential cofactors, mRNA template(s) and amino acids. Use of radiolabelled amino acids in the reaction mixture allows quantitation of incorporation of free amino acid precursors into trichloroacetic acid precipitable proteins.

As shown in FIG. 7, the protein synthesis-inhibitory activity of rTCS produced in *E. coli* and purified to apparent homogeneity, is indistinguishable from that of plant-derived TCS.

Although the invention has been described with reference to specific methods and compositions, it will be apparent to one skilled in the art how various modifications and applications of the methods may be made without departing from the invention.

It is claimed:

1. A cloned nucleic acid which encodes a trichosanthin protein having the functional properties of Trichosanthes-obtained trichosanthin.

2. The nucleic acid of claim 1, wherein said nucleic acid molecule is included in the sequence:

```
       EcoRI
  1  GAATTCAAATATTTTCTGAATAAATATAAAATTCATTGTAGAGAAATGATGAGAA     55
 56  AACAAGAACAATTTTCAAAAACAAAAAATAAAAAACAAATGGTTTATCAAAGAAG    110
111  GCCCGAATTTATTATCAAAAGGCCGAAAGTTAATAATATCTAGGGAAAAACTATT    165
166  ACCTTATAAGAAGCTATTACCTAGATGGCATAAGATCATACTTTTATTTTTGATT    220
221  TAGACTAGAAATACACTAATATATTGTGGACATAGCCAGACAACGATTAGATGGC    275
276  ATACCTCTCTATAAAAACCACAGCTTGAGATGCTCCAATGGCATCCAAATTCCTC    330
331  AAGTCAAAAAG ATG ATC AGA TTC TTA GTC CTC TCT TTG CTA ATT    374
375  CTC ACC CTC TTC CTA ACA ACT CCT GCT GTG GAG GGC GAT GTT    416
417  AGC TTC CGT TTA TCA GGT GCA ACA AGC AGT TCC TAT GGA GTT    458
459  TTC ATT TCA AAT CTG AGA AAA GCT CTT CCA AAT GAA AGG AAA    500
501  CTG TAC GAT ATC CCT CTG TTA CGT TCC TCT CTT CCA GGT TCT    542
543  CAA CGC TAC GCA TTG ATC CAT CTC ACA AAT TAC GCC GAT GAA    584
585  ACC ATT TCA GTG GCC ATA GAC GTA ACG AAC GTC TAT ATT ATG    626
627  GGA TAT CGC GCT GGC GAT ACA TCC TAT TTT TTC AAC GAG GCT    668
669  TCT GCA ACA GAA GCT GCA AAA TAT GTA TTC AAA GAC GCT ATG    710
711  CGA AAA GTT ACG CTT CCA TAT TCT GGC AAT TAC GAA AGG CTT    752
753  CAA ACT GCT GCG GGC AAA ATA AGG GAA AAT ATT CCG CTT GGA    794
795  CTC CCA GCT TTG GAC AGT GCC ATT ACC ACT TTG TTT TAC TAC    836
837  AAC GCC AAT TCT GCT GCG TCG GCA CTT ATG GTA CTC ATT CAG    878
879  TCG ACG TCT GAG GCT GCG AGG TAT AAA TTT ATT GAG CAA CAA    920
921  ATT GGG AAG CGC GTT GAC AAA ACC TTC CTA CCA AGT TTA GCA    962
963  ATT ATA AGT TTG GAA AAT AGT TGG TCT GCT CTC TCC AAG CAA   1004
1005 ATT CAG ATA GCG AGT ACT AAT AAT GGA CAG TTT GAA ACT CCT   1046
1047 GTT GTG CTT ATA AAT GCT CAA AAC CAA CGA GTC ATG ATA ACC   1088
1089 AAT GTT GAT GCT GGA GTT GTA ACC TCC AAC ATC GCG TTG CTG   1130
1131 CTG AAT CGA AAC AAT ATG GCA GCC ATG GAT GAC GAT GTT CCT   1172
1173 ATG ACA CAG AGC TTT GGA TGT GGA AGT TAT GCT ATT TAG TGT   1214
1215 AAC TTC AAG CTA CGT                                       1229
``` where basepairs 411 to 1151 encode the mature form of trichosanthin isolated from *Trichosanthes kirilowii*.

3. The nucleic acid of claim 2, which is derived from basepairs 411 to 1151 and which encodes mature trichosanthin from *Trichosanthes kirilowii*.

4. The nucleic acid of claim 3, which further includes sequences selected from the group consisting of: (a) basepairs 342 to 410, which encodes an amino terminal extension not present in the mature form of TCS; and (b) basepairs 1152–1208, which encodes a carboxyl terminal extension not present in the mature form of TCS.

5. The nucleic acid of claim 2, extending from basepairs 411 to 1151 and further including an expression vector containing a promoter, a ribosome binding site, and an ATG start codon positioned before and adjacent basepair 411, and a stop codon positioned after and adjacent basepair 1151.

6. An expression vector comprising
   (a) a nucleic acid which encodes a trichosanthin protein having the functional properties of Trichosanthes obtained trichosanthin; and
   (b) placing said nucleic acid operatively into an expression vector suitable for expression of the trichosanthin protein in a selected host.

7. The expression vector of claim 6, wherein said nucleic acid is inclined in the sequence:

```
                                             GAT GTT    416
417  AGC TTC CGT TTA TCA GGT GCA ACA AGC AGT TCC TAT GGA GTT    458
459  TTC ATT TCA AAT CTG AGA AAA GCT CTT CCA AAT GAA AGG AAA    500
501  CTG TAC GAT ATC CCT CTG TTA CGT TCC TCT CTT CCA GGT TCT    542
543  CAA CGC TAC GCA TTG ATC CAT CTC ACA AAT TAC GCC GAT GAA    584
585  ACC ATT TCA GTG GCC ATA GAC GTA ACG AAC GTC TAT ATT ATG    626
627  GGA TAT CGC GCT GGC GAT ACA TCC TAT TTT TTC AAC GAG GCT    668
669  TCT GCA ACA GAA GCT GCA AAA TAT GTA TTC AAA GAC GCT ATG    710
711  CGA AAA GTT ACG CTT CCA TAT TCT GGC AAT TAC GAA AGG CTT    752
753  CAA ACT GCT GCG GGC AAA ATA AGG GAA AAT ATT CCG CTT GGA    794
795  CTC CCA GCT TTG GAC AGT GCC ATT ACC ACT TTG TTT TAC TAC    836
837  AAC GCC AAT TCT GCT GCG TCG GCA CTT ATG GTA CTC ATT CAG    878
879  TCG ACG TCT GAG GCT GCG AGG TAT AAA TTT ATT GAG CAA CAA    920
```

-continued

```
921   ATT GGG AAG CGC GTT GAC AAA ACC TTC CTA CCA AGT TTA GCA    962
963   ATT ATA AGT TTG GAA AAT AGT TGG TCT GCT CTC TCC AAG CAA   1004
1005  ATT CAG ATA GCG AGT ACT AAT AAT GGA CAG TTT GAA ACT CCT   1046
1047  GTT GTG CTT ATA AAT GCT CAA AAC CAA CGA GTC ATG ATA ACC   1088
1089  AAT GTT GAT GCT GGA GTT GTA ACC TCC AAC ATC GCG TTG CTG   1130
1131  CTG AAT CGA AAC AAT ATG GCA                                1151
``` which encodes the mature form of trichosanthin isolated from *Trichosanthes kirilowii*.

8. The expression vector of claim 7, wherein the expression vector is an *E. coli* expression vector, and the coding sequence is joined to the ribosome binding site in the vector at a NcoI site which includes the ATG start codon, and is joined at its opposite end at a HindIII site in the vector.

9. The expression vector of claim 7, wherein the expression vector contains a bacterial promoter, a ribosome binding site, and an ATG start codon positioned before and adjacent the amino-terminal codon at position 411, and a stop codon positioned after and adjacent the carboxy terminal codon at position 1151.

* * * * *